US008828935B2

(12) United States Patent
Ishimaru et al.

(10) Patent No.: US 8,828,935 B2
(45) Date of Patent: Sep. 9, 2014

(54) AGENT FOR SUPPRESSING ELEVATION OF BLOOD TRIGLYCERIDE CONCENTRATION

(75) Inventors: Kotomi Ishimaru, Haga-gun (JP); Kazuhisa Sawada, Haga-gun (JP); Akira Shimotoyodome, Haga-gun (JP)

(73) Assignee: KAO Corporation, Tokyo (JP)

( * ) Notice: Subject to any disclaimer, the term of this patent is extended or adjusted under 35 U.S.C. 154(b) by 155 days.

(21) Appl. No.: 13/383,633

(22) PCT Filed: Jul. 16, 2010

(86) PCT No.: PCT/JP2010/062050
§ 371 (c)(1),
(2), (4) Date: Jan. 12, 2012

(87) PCT Pub. No.: WO2011/007863
PCT Pub. Date: Jan. 20, 2011

(65) Prior Publication Data
US 2012/0115779 A1   May 10, 2012

(30) Foreign Application Priority Data

Jul. 16, 2009  (JP) ................................. 2009-168091

(51) Int. Cl.
*A61K 38/00*  (2006.01)
*A61P 3/06*  (2006.01)
*A61K 31/785*  (2006.01)
*C08G 69/10*  (2006.01)

(52) U.S. Cl.
CPC .............. *A61K 31/785* (2013.01); *C08G 69/10* (2013.01)
USPC ............................................ 514/7.4; 514/1.1

(58) Field of Classification Search
None
See application file for complete search history.

(56) References Cited

U.S. PATENT DOCUMENTS

| 4,232,007 | A | 11/1980 | Kajihara et al. | |
| 6,669,971 | B1 * | 12/2003 | Kato et al. | 426/46 |
| 2006/0178343 | A1 | 8/2006 | Shimotoyodome et al. | |
| 2007/0099827 | A1 * | 5/2007 | Uotani et al. | 514/12 |

FOREIGN PATENT DOCUMENTS

| JP | 03-047087 A | 2/1991 |
| JP | 03-290170 A | 12/1991 |
| JP | 05-095767 A | 4/1993 |
| JP | 05-186356 A | 7/1993 |
| JP | 2004-269458 A | 9/2004 |
| JP | 2005-035957 A | 2/2005 |
| JP | 2005-200330 A | 7/2005 |
| JP | 2008-255063 A | 10/2008 |
| JP | 2009-173634 A | 8/2009 |
| WO | WO 2005/049050 A1 | 6/2005 |
| WO | WO 2011/007864 A1 | 1/2011 |
| WO | WO 2011/007865 A1 | 1/2011 |

OTHER PUBLICATIONS

Grundy et al. ("Effectiveness and Tolerability of Simvastatin Plus Fenofibrate for Combined Hyperlipidemia (The SAFARI Trial)"; Am J Cardiol, 2005, pp. 462-468).*
Sung et al., "Natural and Edible Biopolymer Poly-g-glutamic Acid: Synthesis, Production, and Applications", The Chemical Record, 2005, pp. 352-366.*
Ishikawa et al., "Preparation and Characterization of Liposomal Microencapsulated Poly-g-glutamic Acid for Prevention of Ca-Phosphate Precipitation under Intestinal Environment", Food Sci. Technol. Res, 2004, pp. 227-231.*
Yacowitz et al., "Effects of Oral Calcium upon Serum Lipids in Man", British Medical Journal, 1965, pp. 1353-1354.*
Taniguchi et al.,"Natto and viscous vegetables in a Japanese style meal suppress postprandial glucose and insulin responses"; Asia Pac J Clin Nutr 2008, pp. 663-668.*
Extended European search report EP Application No. 10799921.1, including the supplementary European search report and the European search opinion, mailed Dec. 5, 2012, the European Patent Office, Munich, Germany.
Notification of First Office Action for Chinese Patent Application No. 201080031436.7, mailed Sep. 20, 2012, Patent Office of the People's Republic of China, Beijing, China.
International Search Report (ISR) for PCT/JP2010/062050, I.A. fd: Jul. 16, 2010, mailed Sep. 14, 2010, from the Japanese Patent Office, Tokyo, Japan.
International Preliminary Report on Patentability (Chapter I of the Patent Cooperation Treaty) for PCT/JP2010/062050, I.A. fd: Jul. 16, 2010, issued Feb. 7, 2012, from the International Bureau of WIPO, Genera, Switzerland.
Karmaker, S. et al., "Antidiabetic Activity of the Orally Effective Vanadyl-Poly (-Glutamic Acid) Complex in Streptozotocin(STZ)-induced Type 1 Diabetic Mice," J Biomater Appl, 22: 449-464 (Mar. 2008), SAGE Publications, Los Angeles, CA.

* cited by examiner

*Primary Examiner* — Karlheinz R Skowronek
*Assistant Examiner* — Lianko Garyu
(74) *Attorney, Agent, or Firm* — Sterne, Kessler, Goldstein & Fox P.L.L.C.

(57) ABSTRACT

An agent for suppressing elevation of a blood triglyceride concentration, comprising a polyglutamic acid as an active ingredient.

15 Claims, No Drawings

AGENT FOR SUPPRESSING ELEVATION OF BLOOD TRIGLYCERIDE CONCENTRATION

TECHNICAL FIELD

The present invention relates to an agent for suppressing elevation of a blood triglyceride concentration.

BACKGROUND ART

A triglyceride is a kind of a neutral fat, and most of neutral fats containing in blood are triglycerides. It has been known that hypertriglyceridemia and hyperlipidemia are caused by continuing high concentration of triglycerides in blood. Hyperlipidemia has been considered to be the cause of arteriosclerosis, and serve as the initial trigger for inducing disorders such as cardiac disease and cerebral vascular disease.

In general, since changes of blood triglyceride concentrations are strongly affected by diets, complete regulation of the changes of blood triglyceride concentration by using only medicaments is said to be difficult. Therefore, quality of fats ingested as a diet has been focused more than a medical therapy. For example, lowering a blood triglyceride concentration by taking highly-unsaturated fatty acids, such as linoleic acid and linorenic acid, has been recommended. But, on the other hand, since an excessive consumption of the highly-unsaturated fatty acids induces production of overoxidized fatty acids in vivo, possibility of inducing various lifestyle related diseases has been pointed out.

In view of the above situations, to suppress elevation of a blood triglyceride concentration by a safer method which does not induce adverse effects even if administrating or consuming on a daily basis is desired. Recent years, as a substance which suppresses elevation of a blood triglyceride concentration safely and effectively, xanthan gum, propylene glycol alginate ester (see Patent literature 1), chitosan (see Patent literature 2) and a processed starch (see Patent literature 3) which suppress fat absorption have been reported.

Meanwhile, polyglutamic acids are widely used as a moisturizing agent, an absorbing agent and the like due to their high water retaining ability, and gain attentions as highly safe biodegradable polymers. Further, it was reported that polyglutamic acids have an effect of promoting absorption of calcium from the small intestine and an effect of suppressing elevation of a blood pressure (see Patent Literatures 4 and 5).

PRIOR ART LITERATURE

Patent Literatures

Patent Literature 1: JP-A-5-186356 ("JP-A" means unexamined published Japanese patent application)
Patent Literature 2: JP-A-3-290170
Patent Literature 3: JP-A-2004-269458
Patent Literature 4: JP-A-5-95767
Patent Literature 5: JP-A-2008-255063

SUMMARY OF INVENTION

The present invention is contemplated for providing an agent for suppressing elevation of a blood triglyceride concentration, which is useful for medicinal use and food application. Specifically, the present invention is contemplated for providing an agent for suppressing elevation of a blood triglyceride concentration, which suppresses elevation of a triglyceride concentration in blood and is thereby useful for medicinal use or food application as non-medicinal use for decreasing a risk of development of, preventing, improving, alleviating or treating hypertriglyceridemia, hyperlipidemia and arteriosclerosis.

In view of the above-mentioned problem, the present inventors have made extensive studies. As a result, they have found out that polyglutamic acids have an effect of suppressing elevation of a blood triglyceride concentration. The present invention has been completed based on this finding.

The present invention provides the following means.

(1) An agent for suppressing elevation of a blood triglyceride concentration, comprising a polyglutamic acid as an active ingredient.
(2) A polyglutamic acid for use in the suppression of elevation of a blood triglyceride concentration.
(3) A method of suppressing elevation of a blood triglyceride concentration, comprising administering a polyglutamic acid.
(4) Use of a polyglutamic acid for the preparation of a medicament having an effect of suppressing elevation of a blood triglyceride concentration.

EFFECTS OF INVENTION

According to the agent for suppressing elevation of a blood triglyceride concentration of the present invention, elevation of a blood triglyceride concentration, specifically elevation of a blood triglyceride concentration after eating can be suppressed. Furthermore, the agent for suppressing elevation of a blood triglyceride concentration of the present invention regulates a blood triglyceride concentration within a normal range, and is thereby useful for decreasing a risk of development of, preventing, improving, alleviating or treating hypertriglyceridemia, hyperlipidemia, and for suppressing a risk of development of, preventing, improving, alleviating or treating arteriosclerosis.

Other and further features and advantages of the invention will appear more fully from the following description.

MODE FOR CARRYING OUT THE INVENTION

Hereinafter, the present invention is described in detail.

The agent for suppressing elevation of a blood triglyceride concentration of the present invention contains a polyglutamic acid as an active ingredient. The structural formula of the polyglutamic acid used in the present invention is represented by (—NH—CH(COOH)—$CH_2$—$CH_2$—CO—)n.

As shown in the Examples mentioned below, the polyglutamic acid in the present invention has an effect to suppress elevation of a triglyceride concentration in blood. Therefore, the polyglutamic acid can be used as an agent for suppressing elevation of a triglyceride concentration in blood, and can also be used for the preparation of an agent which is for suppressing elevation of a triglyceride concentration.

Until now, it has not been known that a polyglutamic acid has an effect of suppressing elevation of a blood triglyceride concentration. And also, it has not been known that a polyglutamic acid has an effect to prevent or improve hyperlipidemia and arteriosclerosis.

The agent for suppressing elevation of a blood triglyceride concentration of the present invention can be preferably used for suppressing postprandial elevation of a blood triglyceride concentration. As mentioned above, since changes of a blood triglyceride concentration are strongly affected by a meal, it can be expected that a neutral lipid concentration in blood is maintained within a preferable range by, especially, suppressing postprandial elevation of a blood triglyceride concentration. Herein, the term "postprandial" means, specifically, the period after eating foods, beverages and the like, which contain general carbohydrate, fat, etc.

As is shown in the Examples mentioned below, although the effect of the polyglutamic acid to suppress elevation of a blood triglyceride concentration is observed in all over polyglutamic acids regardless of their molecular weights, the polyglutamic acid having a larger molecular weight to some extent shows a more excellent effect of suppressing elevation of a blood triglyceride concentration.

As a result, the molecular weight of polyglutamic acid used in the present invention is preferably a weight average molecular weight of about 9,000 or more, more preferably of 28,000 or more, in order to suppress elevation of a blood triglyceride concentration.

On the other hand, when the agent for suppressing elevation of a blood triglyceride concentration of the present invention is used in the form of an oral liquid preparation, it is preferable that the preparation has a comparatively lower viscosity from the viewpoints of manufacture, smooth feeling, slimy feeling, easiness of swallowing, and the like. Therefore, the upper limit of the weight average molecular weight of the polyglutamic acid is preferably about 5,000,000, more preferably about 800,000. Therefore, from the viewpoints of an effect of suppressing elevation of a blood triglyceride concentration, the weight average molecular weight of the polyglutamic acid is preferably from 9,000 to 5,000,000, more preferably from 28,000 to 5,000,000. From the viewpoint of viscosity, the weight average molecular weight of the polyglutamic acid is preferably from 9,000 to 5,000,000, more preferably from 9,000 to 800,000. From both of the viewpoints of an effect of suppressing elevation of a blood triglyceride concentration and of viscosity, the weight average molecular weight of the polyglutamic acid is preferably from 9,000 to 5,000,000, more preferably from 28,000 to 800,000. The weight average molecular weight can be measured by, for example, high performance liquid chromatography using a gel permeation column.

The polyglutamic acid used in the present invention can be produced by a chemical synthesis and can be also generated by a microorganism, and a commercial product can also be used. Furthermore, the optical activity of glutamic acid that constitutes the polyglutamic acid may be a D- or L-form, or a mixture thereof. A natural polyglutamic acid is a polymer that is formed by binding of glutamic acid at the γ-position, and it can be obtained by culturing wild type microorganisms having an ability to produce a polyglutamic acid, or microorganisms given an ability to produce a polyglutamic acid by gene recombination, or the like. Examples of wild type microorganisms that produce a polyglutamic acid may include a part of *Bacillus* including *Bacillus subtilis* var. *natto* and related species thereof (*Bacillus subtilis* var. *chungkookjang, Bacillus licheniformis, Bacillus megaterium, Bacillus anthracis, Bacillus halodurans*), *Natrialba aegyptiaca, Hydra* and the like (Ashiuchi, M., et al.: Appl. Microbiol. Biotechnol., 59, pp. 9-14 (2002)). As examples of the production of a polyglutamic acid using a gene recombination technique, it is known that a producibility of about 9 g/L/5 days is obtained in a recombinant *Bacillus subtilis* that has been gene-transferred with a plasmid (*Bacillus subtilis*, ISW1214 strain) (Ashiuchi, M., et al.: Biosci. Biotechnol. Biochem., 70, pp. 1794-1797 (2006)) and a producibility of about 4 g/L/1.5 days is obtained in a recombinant *E. coli* that has been gene-transferred with a plasmid (Jiang, H., et al.: Biotechnol. Lett., 28, pp. 1241-1246 (2006)). Furthermore, polyglutamic acids are commercially produced as food additives, materials for cosmetics, thickening agents, and the like, and it is also possible to purchase polyglutamic acids that are supplied by domestic or foreign manufacturers of polyglutamic acids (for example, domestic manufacturers: Nippon Poly-Glu Co., Ltd., Ichimaru Pharcos Co., Ltd., Meiji Food Materia Co., Ltd. and the like, foreign manufacturers: BioLeaders Corporation and the like).

Further, the polyglutamic acid may be a salt thereof in the present invention. In this case, examples of the salt may include alkali metal salts such as sodium salts and potassium salts, alkaline earth metal salts such as magnesium salts and calcium salts, ammonium salts, ethanolamine salts, basic amino acid salts and the like, and the salt is not specifically limited as long as it can be used for medical or food application.

In the present invention, the above-mentioned polyglutamic acid can be used as an agent for suppressing elevation of a blood triglyceride concentration itself. Alternatively, the polyglutamic acid may be used after adding a suitable liquid or solid excipient or bulking agent such as titanium oxide, calcium carbonate, distilled water, lactose and starch. In this case, although the content of the polyglutamic acid is not specifically limited, it is included by preferably from 0.01 to 100% by mass, specifically preferably from 0.1 to 80% by mass in the agent for suppressing elevation of a blood triglyceride concentration.

When the agent for suppressing elevation of a blood triglyceride concentration is used for use in foods, medicaments or the like, the polyglutamic acid can be solely administered to humans and animals by gastrointestinal administration, intraperitoneal administration, intravascular administration, intradermal administration, subcutaneous administration or the like, or can be ingested as a form of various foods, medicinal products, pet foods or the like, all of which incorporates the polyglutamic acid. As the food, it is possible to apply to general foods, as well as to foods such as cosmetic foods, foods for diseased persons and foods for specified health use, which have the concepts of decreasing the risk of development of, preventing, improving, alleviating or treating hypertriglyceridemia, hyperlipidemia and arteriosclerosis. In the case of use as a medicinal product, the agent can be formed into an oral solid formulation such as a tablet and a granule agent, or an oral liquid formulation such as an internal liquid agent and a syrup agent.

Meanwhile, when an oral solid formulation is to be prepared, a tablet, a coated tablet, a granular agent, a powder agent, a capsule agent or the like can be produced by a conventional method after adding an excipient, and if needed, a binder, a disintegrating agent, a lubricating agent, a coloring agent, a taste masking agent, a flavoring agent and the like to a polyglutamic acid. Alternatively, when an oral liquid formulation is to be prepared, an oral liquid agent, a syrup agent, an elixir agent or the like can be prepared by a conventional method by adding a taste masking agent, a buffering agent, a stabilizer, a taste masking agent and the like.

Although the content of the polyglutamic acid to be incorporated in each of the above-mentioned agents is not specifically limited, the content is preferably from 0.01 to 100% by mass, specifically preferably from 0.1 to 80% by mass.

The effective administration (ingestion) amount of polyglutamic acid in each of the above-mentioned agents is preferably from 0.01 g/kg body weight to 1.0 g/kg body weight per day. Further, the agent for suppressing elevation of a blood triglyceride concentration of the present invention is preferably used before or during eating.

Although a subject of administration or ingestion is not specifically limited as long as the subject is a person in need thereof, a person having a fasting blood triglyceride level of 100 mg/dL or more.

EXAMPLES

Hereinafter, the present invention will be described more in detail with reference to Examples, but the present invention is not limited thereto.

Preparation Example 1

Preparation of Polyglutamic Acid Having Weight Average Molecular Weight of 190,000

Using a commercially available polyglutamic acid having weight average molecular weight of 800,000 (manufactured by Meiji Food Materia Co., Ltd.) as a starting material, 500 mL of a 3 (w/w) % aqueous solution of the polyglutamic acid was prepared. Then, the pH of this solution was adjusted to 2 with hydrochloric acid, and the temperature was set to constant at 70° C. At 3 hours after the initiation of the setting to a constant temperature, the solution was neutralized to pH 7 by using an aqueous sodium hydroxide solution, and concentrated by using an ultrafiltration membrane having an exclusion limit of 300 k (type: PBNK, manufactured by Millipore). At that time, washing by adding water was suitably conducted with distilled water of a three-fold amount of the sample before concentration, and a 10-fold concentrate was subjected to lyophilization. The molecular weight of the sample after lyophilization was determined by an HPLC method as shown in the measurement examples mentioned below. As a result, 1.7 g of a polyglutamic acid having a weight average molecular weight of 190,000 was obtained.

Preparation Example 2

Preparation of Polyglutamic Acid Having Weight Average Molecular Weight of 70,000

Using a commercially available polyglutamic acid having weight average molecular weight of 800,000 (manufactured by Meiji Food Materia Co., Ltd.) as a starting material, 500 mL of a 3 (w/w) % aqueous solution of the polyglutamic acid was prepared. Then, the pH of this solution was adjusted to 2 with hydrochloric acid, and the temperature was set to constant at 70° C. At 6 hours after the initiation of the setting to a constant temperature, the solution was neutralized to pH 7 by using an aqueous sodium hydroxide solution, and concentrated by using an ultrafiltration membrane having an exclusion limit of 100 k (type: PBHK, manufactured by Millipore). At that time, washing by adding water was suitably conducted with distilled water of a three-fold amount of the sample before concentration, and a 10-fold concentrate was subjected to lyophilization. The molecular weight of the sample after lyophilization was determined by an HPLC method as shown in the measurement examples mentioned below. As a result, 8.3 g of a polyglutamic acid having a weight average molecular weight of 70,000 was obtained.

Preparation Example 3

Preparation of Polyglutamic Acid Having Weight Average Molecular Weight of 28,000

Using a commercially available polyglutamic acid having a weight average molecular weight of 800,000 (manufactured by Meiji Food Materia Co., Ltd.) as a starting material, 500 mL of a 3 (w/w) % aqueous solution of the polyglutamic acid was prepared. Then, the pH of this solution was adjusted to 2 with hydrochloric acid, and the temperature was set to constant at 70° C. At 8 hours after the initiation, the temperature was changed to 90° C. At 11 hours after the initiation of the setting to a constant temperature, the solution was neutralized to pH 7 by using an aqueous sodium hydroxide solution, and concentrated by using an ultrafiltration membrane having an exclusion limit of 50 k (type: PBQK, manufactured by Millipore). At that time, washing by adding water was suitably conducted with distilled water of a three-fold amount of the sample before concentration, and a 10-fold concentrate was subjected to lyophilization. The molecular weight of the sample after lyophilization was determined by an HPLC method as shown in the measurement examples mentioned below. As a result, 6.3 g of a polyglutamic acid having a weight average molecular weight of 28,000 was obtained.

Quantification and Molecular Weight Determination of Polyglutamic Acid

The quantification and molecular weight of the polyglutamic acid were performed by using an HPLC analysis using TSKGel G4000PWXL and TSKGel G6000PWXL gel permeation columns (trade names, manufactured by Tosoh Corporation). The analysis conditions were that 0.1 M sodium sulfate was used as an eluant, and that the flow rate was 1.0 mL/min, the column temperature was 50° C. and the UV detection wavelength was 210 nm. For verification of concentrations, a calibration curve was prepared by using a polyglutamic acid having a molecular weight of 800,000 (manufactured by Meiji Food Materia Co., Ltd.). Further, for verification of molecular weights, polyglutamic acids having various different molecular weights (those manufactured by Wako Pure Chemical Industries, Ltd. (162-21411 and 162-21401)), SIGMA-ALDRICH (P-4886 and P-4761) and Meiji Food Materia Co., Ltd. (molecular weight: 880,000)), weight average molecular weights of which had been obtained in advance by using pullulan (trade name: Shodex STANDRD P-82, manufactured by Showa Denko K.K.), were used.

Test Example 1

Effect of Polyglutamic Acid to Suppress Elevation of Blood Triglyceride Concentration As polyglutamic acids (PGAs), six kinds of samples having weight average molecular weights of 9,000, 350,000 and 800,000 (manufactured by Meiji Food Materia Co., Ltd.) and of 28,000, 70,000 and 190,000 (prepared in Preparation Examples 1 to 3) were used.

Furthermore, the following experiments were performed by using eight 8-week-old male mice (C57BL/6J Jcl: manufactured by Clea Japan, Inc.) for each group.

1. Preparation of Oral Administration Samples

An emulsion liquid was prepared by emulsifying glucose (manufactured by Kanto Kagaku) and triolein (Glyceryl trioleate: manufactured by Sigma) by using lecithin (made from eggs, manufactured by Wako Pure Chemical Industries) and albumin (derived from bovine serum, manufactured by Sigma). A sample for oral administration was prepared by adding the polyglutamic acid sample to this emulsion liquid so that the final concentrations became 5 (w/w) % of the polyglutamic acid, 5 (w/w) % of glucose, 5 (w/w) % of triolein, and 0.2 (w/w) % of lecithin and 1.0 (w/w) % of albumin in the emulsifying agent. Furthermore, a sample in which water had been added instead of the polyglutamic acid was prepared as a control sample.

2. Oral Administration Tests

The initial blood sampling was performed on a mouse that had been food-deprived overnight by using a heparin-treated hematocrit capillary (manufactured by VITREX) from the orbital vein under ether anesthesia. Thereafter, the oral administration sample was administered orally by using a feeding needle, and the blood was collected from the orbital vein under ether anesthesia at after 10 minutes, 30 minutes, 1 hour and 2 hours. The amount of oral administration against the mouse is shown in the following Table 1.

TABLE 1

Amount of oral administration in mouse

| | Glucose (mg/1 g body weight) | Triolein (mg/1 g body weight) | Polyglutamic acid (mg/1 g body weight) |
|---|---|---|---|
| Control group | 2 | 2 | — |
| Polyglutamic acid administered group | 2 | 2 | 2 |

The blood collected by the heparin-treated hematocrit capillary was stored under ice-cooling until plasma separation, and centrifuged at 11,000 rpm for 5 minutes to give plasma. A blood triglyceride concentration in the obtained plasma was measured by using triglyceride E-test Wako (manufactured by Wako Pure Chemical Industries, Ltd., GPO•DAOS method).

Based on the results of the measurement of the blood triglyceride concentrations up to 2 hours after the oral administration of the sample, the difference (Δ value) between the maximum value (at 30 minutes or 1 hour after the administration) and the initial value (at the time of the initial blood sampling) of the blood triglyceride concentration was defined as the maximum triglyceride concentration elevation, and is shown in Table 2.

Further, the statistically-significant difference between the groups was also considered based on the obtained values of the maximum triglyceride concentration elevation, and is shown in Table 2. When significance (p<0.05) was recognized by an analysis of variance, significant difference between the groups was determined by a verification between the polyglutamic acid-administered groups (weight average molecular weights: 9,000, 28,000, 70,000, 190,000, 350,000 and 800,000) and the control group using a multiple comparison test (Bonferroni/Dunn method). From the obtained result, significance was judged with considering p<0.05 as a significant difference.

TABLE 2

Maximum triglyceride concentration elevation in mouse
(maximum value − initial value)
(analysis of variance P < 0.05)

| | Maximum triglyceride concentration elevation Average ± S.E. | Significant difference from control group |
|---|---|---|
| Control group | 95.4 ± 20.1 | — |
| Polyglutamic acid (weight average molecular weight of 9,000) group | 78.4 ± 32.6 | N.S. |
| Polyglutamic acid (weight average molecular weight of 28,000) group | 47.6 ± 16.4 | P < 0.05 |
| Polyglutamic acid (weight average molecular weight of 70,000) group | 48.8 ± 13.1 | P < 0.05 |
| Polyglutamic acid (weight average molecular weight of 190,000) group | 27.4 ± 11.7 | P < 0.05 |
| Polyglutamic acid (weight average molecular weight of 350,000) group | 7.1 ± 11.7 | P < 0.05 |
| Polyglutamic acid (weight average molecular weight of 800,000) group | 25.9 ± 5.0 | P < 0.05 |

*) S.E.: Standard Error
*) N.S.: Not Significant

As is apparent from the results shown in Table 2, the maximum triglyceride concentration elevation was lower than that of the control group in all of the polyglutamic acids (weight average molecular weights: 9,000, 28,000, 70,000, 190,000, 350,000 and 800,000). Further, the maximum triglyceride concentration elevation was significantly lower than that of the control group in the polyglutamic acids having weight average molecular weights of 28,000, 70,000, 190,000, 350,000 and 800,000, and thus it was found that a polyglutamic acid having a higher molecular weight has a more excellent effect of suppressing the elevation of triglyceride.

Further, as mentioned above, it is known that elevation of a blood triglyceride induces hyperlipidemia, followed by arteriosclerosis. Therefore, the above-mentioned polyglutamic acids can be preferably used for the prevention and improvement of hyperlipidemia and arteriosclerosis, by effectively suppressing elevation of a blood triglyceride concentration.

INDUSTRIAL APPLICABILITY

The agent for suppressing elevation of a blood triglyceride concentration of the present invention has functions to decrease a risk of development of, prevent, improve, and alleviate hyperlipidemia and arteriosclerosis. Therefore, the present invention can be utilized in the fields of functional foods, medicinal products and medical treatments.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2009-168091 filed in Japan on Jul. 16, 2009, which is entirely herein incorporated by reference.

The invention claimed is:
1. A method of suppressing elevation of postprandial blood triglyceride concentration in a subject having a fasting blood triglyceride level of 100 mg/dL or more, comprising administering to said subject an effective amount of polyglutamic acid, wherein the polyglutamic acid has a weight average molecular weight of 190,000 to 5,000,000, wherein said polyglutamic acid is administered in a solid or liquid composition that either consists of polyglutamic acid or comprises a polyglutamic acid formulation, and wherein said effective amount is 0.01 grams (g) to 2 grams (g) of polyglutamic acid per kilogram (kg) body weight of said person per day.

2. The method of claim 1, wherein said polyglutamic acid has a weight average molecular weight of 190,000 to 800,000.

3. The method of claim 1, wherein said polyglutamic acid has a weight average molecular weight of 190,000 to 350,000.

4. The method of claim 1, wherein said polyglutamic acid has a weight average molecular weight of 190,000.

5. The method of claim 1, wherein said polyglutamic acid has a weight average molecular weight of 350,000.

6. The method of claim 1, wherein said polyglutamic acid has a weight average molecular weight of 350,000 to 800,000.

7. The method of claim 1, wherein said polyglutamic acid is administered in the form of an oral liquid preparation.

8. The method of claim 1, wherein said polyglutamic acid is administered in the form of a food.

9. The method of claim 1, wherein said polyglutamic acid administered in the form of an oral solid formulation.

10. The method of claim 1, wherein said subject is a human.

11. The method of claim 1, wherein said subject is a non-human animal.

12. The method of claim 1, wherein said polyglutamic acid is ingested.

13. The method of claim 12, wherein said polyglutamic acid is ingested in an amount from 0.01 to 1.0 g/kg body weight per day.

14. The method of claim 1, wherein said administering occurs during or before eating.

15. The method of claim 14, wherein said administering occurs during said eating.

* * * * *